United States Patent [19]

Weil

[11] 4,005,034
[45] Jan. 25, 1977

[54] POLY(HALOETHYL-ETHYLENEOXY) PHOSPHORIC ACID ESTER POLYMERS AS FLAME RETARDANT AGENTS

[75] Inventor: Edward D. Weil, Hastings-on-Hudson, N.Y.

[73] Assignee: Stauffer Chemical Company, Westport, Conn.

[22] Filed: Dec. 20, 1974

[21] Appl. No.: 535,004

Related U.S. Application Data

[60] Division of Ser. No. 409,486, Oct. 25, 1973, Pat. No. 3,896,187, Continuation-in-part of Ser. No. 164,928, July 21, 1971, abandoned, Continuation-in-part of Ser. No. 760,988, Sept. 19, 1968, abandoned.

[52] U.S. Cl. .......................... 260/2.5 AJ; 106/177; 260/45.7 P; 260/77.5 SS; 260/865
[51] Int. Cl.² ...................... C08K 5/51; C08K 5/52; C08J 9/52
[58] Field of Search .................. 260/2.5 AJ, 45.7 P; 106/177

[56] References Cited

UNITED STATES PATENTS

| | | | |
|---|---|---|---|
| 2,733,226 | 1/1956 | Hunter | 260/29.7 |
| 3,027,349 | 3/1962 | Bahr et al. | 260/45.7 |
| 3,262,894 | 7/1966 | Green | 260/2.5 |
| 3,361,691 | 1/1968 | Mazzeo | 260/23.7 |
| 3,515,565 | 6/1970 | Wood et al. | 106/177 |
| 3,701,816 | 10/1972 | Nogami et al. | 260/927 |
| 3,836,507 | 9/1974 | Yoshizawa et al. | 260/64 |

OTHER PUBLICATIONS

Gefter, "Organophosphorus Monomers and Polymers," 1962, p. 208.

Primary Examiner—Lewis T. Jacobs
Assistant Examiner—R. A. White
Attorney, Agent, or Firm—Paul J. Juettner

[57] ABSTRACT

Liquid poly(haloethyl-ethyleneoxy) phosphoric acid esters are prepared by condensing tris (2-haloethyl) phosphate at a temperature of from 140° C. to 220° C. in the presence of a catalyst until from about 0.5 to about 0.9 moles of ethylene dihalide per mole of tris(2-haloethyl) phosphate is evolved. A low acidity product is obtained. Any residual acidity in the product is substantially eliminated by neutralization with an alkylene oxide.

6 Claims, No Drawings

POLY(HALOETHYL-ETHYLENEOXY) PHOSPHORIC ACID ESTER POLYMERS AS FLAME RETARDANT AGENTS

The present application is a division of application Ser. No. 409,486, filed Oct. 25, 1973, now U.S. Pat. No. 3,896,187, issued July 22, 1975, said application Ser. No. 409,486 being a continuation-in-part of application Ser. No. 164,928, filed July 21, 1971, now abandoned, said application Ser. No. 164,928 being a continuation of parent application Ser. No. 760,988, filed Sept. 19, 1968, and now abandoned.

The present invention relates to halogen containing organophosphorus polymers and to their method of preparation from tris(2-haloethyl) phosphates. The products of the invention which can be termed poly (haloethyl-ethyleneoxy) phosphoric acid esters are flame retardant agents particularly for use in polyurethane compositions and cellulose acetate films.

Tris(2-haloethyl phosphates and particularly tris(2-chloroethyl) phosphate are known compounds, the chloro derivative being a known flame retardant agent for polyurethane foams. It is also known in the prior art that the chloro compound will undergo polycondensation with the splitting out of ethylene dichloride to form solid polymers. These solid polymers are prepared, in accordance with the procedure of German Patent No. 1,202,501, by heating tris(2-chloroethyl) phosphate at a temperature within the range of 190° C. to about 240° C. in the presence of a basic catalyst until about one mole of ethylene dichloride per mole of tris(2-chloroethyl) phosphate is generated.

Liquid polycondensed polymers of tris(2-chloroethyl) phosphate have also been prepared by heating the phosphate to temperatures within the range of from 240° C. to 280° C. (Korshak et al, Bull, Acad. Sci. USSR, Chem. Section, 1958, pp. 196–201). This reaction at this temperature is complex and uncontrollable. The products are dark, viscous, fluids which are highly acidic. The acidity makes the products undesirable for use as flame retardant agents for polyurethane prepared by normal procedures using the monomer amine catalyst system in that the high acidity tends to neutralize the catalyst, and their color reduces their usefulness as flame retardants for most plastics.

It has now been found that liquid polycondensation products of tris(2-haloethyl) phosphate and, particularly tris(2-chloroethyl) phosphate can be easily prepared by a carefully controlled polycondensation reaction to yield substantially clear, colorless polymeric products which are useful as flame retardant additives, particularly for polyurethane foams.

In accordance with the present invention, liquid poly(haloethyl-ethyleneoxy) phosphoric acid esters are provided by heating a 2-haloethyl phosphorus compound reaction mixture containing a major proportion (at least 50%) of tris(2-haloethyl) phosphate and a minor proportion of other esters of phosphorus having at least one 2-haloethyl substituent to a temperature within the range of from about 140° C. to about 200° C. in the presence of a basic catalyst for a period of time sufficient to generate reaction by-product ethylene dihalide in an amount of from about 0.5 mole to about 0.9 mole per mole of 2-haloethyl phosphorus compound. The products are clear liquids and can have varying degrees of polymerization and viscosity depending on the amount of ethylene dihalide generated during the polycondensation reaction which can be controlled by adjustment of reaction conditions. The products are extremely low in acid content though any residual acid content can be substantially eliminated by post treating the reaction product with an acidity neutralizing agent such as an alkylene oxide at a temperature ranging from ambient to the polymerization temperature. The products can be effectively used as flame retardant additives for polyurethane foam. Particularly, the products of the present invention can unexpectedly provide flame retardant properties using smaller amounts and correspondingly at lower phosphorus and chlorine levels than that required to provide similar flame retardant properties using tris(2-haloethyl) phosphate alone. This is surprising inasmuch as the quantity of phosphorus and chlorine in the additive is generally determinative of the effectiveness of the additives as a flame retardant.

Tris(2-haloethyl) phosphates are a known class of compounds which can be easily prepared by known methods. These compounds are preferably the chloro or bromo derivatives. The term tris(2-haloethyl) phosphate is also intended to include mixed halo derivatives and also mixtures of derivatives as well as pure tris compounds themselves. Preferably, the chloro derivatives are utilized in the form of tris(2-chloroethyl) phosphate.

The tris(2-haloethyl) phosphate constitutes the major proportion of the reaction mixture used in the polycondensation reaction of the present invention. Preferably, the reaction mixture is constituted solely of the tris(2-haloethyl) phosphate compound though the reaction mixture can also contain a minor proportion, i.e., from 0% to about 50% by weight of another ester of phosphoric acid having at least one 2-haloethyl substituent thereon. As with the tris esters, the 2-chloroethyl derivative is preferred. The remaining ester groups can be any organic radicals which do not interfere with the polycondensation reaction and these can be illustrated by lower alkyl groups of from 1 to 10 carbon atoms, aryl, such as phenyl; substituted alkyl; arylalkyls, e.g., benzyl and α-methylbenzyl; substituted aryls, such as alkaryl, e.g., tolyl, xylenyl, isopropylphenyl t-butylphenyl and chlorophenyl; haloalkyls, such as chloroisopropyl, dichloroisopropyl, bromochloroisopropyl, and 2,3-dibromopropyl; and the like. These are given as illustrative and are in no way intended to be inclusive of all such compounds.

The polycondensation reaction is conducted in the presence of a basic catalyst. Suitable bases include alkali metal and alkaline earth metals, such as sodium, potassium, magnesium, calcium and the like; their oxides, such as sodium oxide, potassium oxide, magnesium oxide, calcium oxide, and the like; hydroxides, such as sodium hydroxide, potassium hydroxide, magnesium hydroxide, calcium hydroxide and the like; carbonate and bicarbonates, such as sodium carbonate and bicarbonate potassium carbonate and bicarbonate, magnesium carbonate and bicarbonate, calcium carbonate and bicarbonate and the like; alkoxides, such as sodium ethoxide, potassium ethoxide, magnesium ethoxide, calcium ethoxide, and the like; phenolates, such as sodium phenolate, potassium phenolate, magnesium phenolate, calcium phenolate, and the like, and salts of strong bases and weak acids such as alkali metal and alkali earth metal acetates, and phosphates, and salts of organic phosphorus acids and partial phosphate esters. Organic bases such as amines, for example, pyridine, quinoline, triethylamine, tetramethylguanidine, N-methylmorpholine, butylamine, aniline, and the like may be used. The definition of bases in the context of the present invention extends to those substances known as "Lewis bases," that is, electron pair donors, and thus includes, for example, trialkylphosphines, triphenyl phosphines, tributyltin oxide and the like. The true catalyst is believed to be the anion of a salt of bis(2-haloethyl) phosphate prepared in situ by the cleavage of tris(2-haloethyl) phosphate with a salt whose anion is sufficiently nucleophilic to effect the cleavage. Thus, substances not normally considered bases such as alkali metal halide, e.g., sodium chloride, sodium bromide, and the like, potassium chloride, potassium bromide, and the like, are included within the term basic catalyst as used herein inasmuch as they are sufficiently nucleophilic to effect the desired cleavage. Suitable quantities of base for catalytic purposes are from a few parts per million, e.g., 50 p.p.m. up to about 10% by weight, preferably 0.01–5% by weight, based on the weight of the reaction mixture.

The base catalyst can be liquid or solid, as desired. Suitable solid basic compounds are alkali and alkaline earth metals and their salts, such as sodium or potassium hydroxide, sodium or potassium carbonate or bicarbonate, sodium alcoholate, and finely divided metallic sodium or potassium. The addition of the solid basic compound or alkali metal is accomplished by stirring the tris(2-haloethyl) phosphate with solid sodium or potassium hydroxide as pellets or flakes or with coarsely pulverized alkali carbonate or finely divided metallic sodium or potassium at room temperature 0.01–5% by weight of solid basic compound or alkali metal, calculated on the tris(2-haloethyl) phosphate, is stirred in. The amount of solid basic compound or alkali metal thus dissolved can be determined by a simple titration.

The reaction mixture is then heated to a temperature within the range of from about 140° C. to about 200° C., and preferably from about 170° C. to about 220° C. for a period of time sufficient to generate by-product ethylene dihalide in an amount of from about 0.5 mole to about 0.9 mole ethylene dihalide per mole of 2-haloethyl phosphorus compound. The heating can be conducted in any type of appropriate reaction vessel, preferably a reaction vessel having a distillation apparatus attached thereto. The amount of ethylene dihalide formed during the polycondensation reaction can be easily determined by stripping the byproduct ethylene dihalide as it is formed during the reaction and determining the amount obtained until such time as the desired reaction end point is reached, at which point the reaction can be terminated.

The amount of ethylene dihalide formed during the polycondensation reaction is an indication of the degree of condensation. After generation of approximately 0.5 mole ethylene dihalide per mole of 2-haloethyl phosphorus compound, a product having an average molecular structure of the dicondensation product is obtained. After approximately 0.9 mole ethylene dihalide has been liberated, or generated within the reaction mixture, the product has an average degree of condensation of approximately 10. By controlling the amount of ethylene dihalide generated within the range of from about 0.5 mole to about 0.9 mole per mole of 2-haloethyl compound products of various viscosities having relative degrees of polymerization of from approximately 2 to about 10 can be prepared. For the preferred product, i.e., the polycondensate of tris(2-chloroethyl) phosphate, the reaction is conducted until ethylene dichloride in amounts of from about 17.5% to about 31% by weight based on the total weight of the reaction mixture is evolved. This corresponds to the 0.5 to 0.9 mole ethylene dichloride per mole of tris(2-chloroethyl) phosphate used to prepare the product.

The products of the invention are characterized by low acid numbers though any residual acid content can be substantially eliminated by post treating the reaction product with an acidity neutralizing agent such as an alkylene oxide. Any alkylene oxide can be used. Alkylene oxide is broadly intended to include any compound having an oxirane group (i.e.,

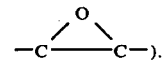

Illustrative of these compounds are ethylene oxide, propylene oxide, butylene oxide, styrene oxide, epichlorohydrin, epibromohydrin, diglycidyl ether, glycidyl butyl ether, glycidyl alkyl ether, glycidyl ether or phenol, diglycidyl ether of resorcinol, glycidyl ether of cresol and brominated cresol, glycidyl esters of acids such as acetic, acrylic and methacrylic acid, glycidol, diglycidyl ethers of bisphenol A and related epoxy resins made from bisphenol, or tetrahalobisphenols and epichlorohydrin, diepoxide dicyclopentylene ether, the diepoxide of vinylcyclohexene, the diepoxide of cyclohexenylmethyl cyclohexanecarboxylate, diepoxide of bis(cyclohexenylmethyl) adipate, and the like. The alkylene oxide is used in an amount sufficient to neutralize acidity, generally from about 0.05 to about 5% by weight based on the total weight of the product. When a gaseous epoxide, such as ethylene oxide, is employed, it may conveniently be passed in and through the reaction product until neutralization is achieved. The unreacted excess which passes through can, if desired, be collected and recycled. Neutralization can be accomplished at any temperature from ambient to the polycondensation temperature, i.e., about 20° C. to about 140° C.

The following examples illustrate the process of the present invention.

EXAMPLE 1

A mixture of 428.2 grams (1.5 mole) of tris(2-chloroethyl) phosphate is heated to 190° C. to 200° C. in the presence of 2.1 grams of sodium carbonate catalyst. The mixture is held at this temperature for 1.3 hours until 77 grams of ethylene dichloride is distilled off. Vacuum stripping at 100° C. removes another 12 grams of ethylene dichloride totalling 89 grams (0.9 mole) or approximately 20.8% (0.6 mole ethylene dichloride per mole of tris(2-chloroethyl) phosphate). The product is a nearly colorless liquid, having an acid content of 0.18 milliequivalents per gram (titration to Congo Red end point). By heating the product at 100° C. with 5 grams of epichlorohydrin, this acidity is eliminated.

EXAMPLE 2

The procedure of Example 1 is repeated with an extension of the heating time so that 109 grams (1.1 mole) or approximately 25.5% by weight of ethylene dichloride is liberated. The product is found to have 0.2 milliequivalent of acid per gram. Treatment with 3 grams of epichlorohydrin at 100° C. reduces this acidity. The acidity can be substantially eliminated by adding 8 grams of the diepoxide of cyclohexenylmethyl cyclohexene carboxylate to the product and allowing the product to stand at 25°–30° C. for 10 days.

EXAMPLE 3

The procedure of Example 1 is repeated with an extension of the heating time until approximately 31% ethylene dichloride is liberated. The product is a highly viscous liquid which gels on further heating.

EXAMPLE 4

Mixtures of 856.4 grams (3 mole) of tris(2-chloroethyl) phosphate were heated to 150° C, 160° C., and 170° C. in the presence of 0.97 grams of sodium carbonate catalyst. The ethylene dichloride given off in the reaction and from vacuum stripping the final product were collected. The following results were obtained:

TABLE I

| SAMPLE NO. | | 1 | 2 | 3 | 4 | 5 |
|---|---|---|---|---|---|---|
| Tris(2-chloroethyl) Phosphate (CEF) (Moles) | | 3 | 3 | 3 | 3 | 3 |
| Reaction Temperature (° C.) | | 150 | 150 | 160 | 170 | 170 |
| Reaction Time (hours) | | 31 | 34 | 20 | 6.5 | 9.5 |
| Ethylene dihalide evolved | grams | 189.3 | 195.6 | 201.6 | 180.1 | 200.2 |
| | Moles/mole (CEF) | .64 | .66 | .67 | .63 | .67 |
| Product Viscosity (Cps. 25° C.) | | 910 | — | 3,330 | 447 | 1,840 |
| Acid Numbers* | | | | | | |
| H₂O-Acetone, 20 min. | | 19.0 | 18.1 | 28.5 | 21.0 | 33.8 |
| MeOH-Acetone, 20 min. | | 3.7 | 13.4 | 4.7 | 2.8 | 10.6 |

*Determined after a 20 minute wait period following dissolution using methyl red as indicator. Acid numbers are expressed as milliequivalent per gram (titration to methyl red end point).

The products were neutralized by bubbling ethylene oxide with stirring into and through the reaction mixture at 90°–100° C., until a satisfactorily low acid number (i.e., practical neutrality) was achieved. The following viscosity and acidity readings were obtained:

TABLE II

| SAMPLE NO. | 1 | 2 | 3 | 4 | 5 |
|---|---|---|---|---|---|
| Viscosity CPS-25° C. | 1525 | 5300 | — | 584 | 7600 |
| Acid Number H₂O-Acetone, 20 min | | | | | |
| Before Treatment | 19.0 | 18.1 | 28.5 | 21.0 | 33.8 |
| After Treatment | 0.17 | 0.39 | — | 0.33 | 0.39 |

The products of the present invention are clear liquids which are low in acid values which products are extremely useful as flame retardant agents for polyurethane foams. The compounds can be used alone or in various admixtures with other known flame retardant agents presently in use in the production of flame resistant polyurethane foams. The exact amount of the compounds to be used depends on the foam density, composition and degree of flame retarding required in the polyurethane foam. An effective amount for general purposes has been found to be within the range of from about 2% to about 30% by weight. Specific applications may require amounts outside this range and this range is given only as a specific illustration of the manner in which the present invention can be utilized.

The production of urethane or isocyanate polymers is a well known commercial process, see for instance Kirk-Othmer, The Encyclopedia of Chemical Technology, First Supplement, pages 888 et seq. (Interscience 1957). Briefly, this process involves the reaction of an isocyanate and a second compound which may contain an hydroxyl, amino or carboxy group, i.e., a compound containing active hydrogen. A preferred group of compounds containing active hydrogen are the di- or polyfunctional hydroxy compounds. As used in this specification the term "isocyanate material" is intended to include isocyanate or urethane compositions containing unreacted -NCO radicals.

The most common polymers are formed by the reaction of toluene diisocyanate (hereafter TDI) and a saturated polyester. (This latter compound may, however, contain benzene unsaturation.) Representative polyesters are the reaction products of adipic acid and/or phthalic anhydride and ethylene glycol. For purposes of simplicity in the following specification and claims, this type of polyester will be identified simply by the term "phthalicadipic acid type polyester." Other compounds which may be used in place of the polyesters are polyethers, simple glycols, polyglycols, castor oil, drying oils, etc. Whether the products are to be flexible or rigid depends upon the degree of cross-linking and thus the type of polyol which is used. Since the products of this invention may replace only a part of the polyol, they are thus suitable for use in either flexible or rigid foams.

When an expanded or foamed product is to be produced, it is the general practice to add water to the composition. The water reacts with the -NCO groups to release $CO_2$ and cause the expansion of the polymer into a foamed mass.

Control of this reaction requires considerable skill and often special equipment. In some cases it has been found advisable to use inert dissolved gasses including the various halohydrocarbons such as the well known Freons or Genetrons. These low boiling liquids boil when warmed by the heat of reaction and thus cause foaming. They also serve to lower the thermal conductivity and increase the flame resistance of the resulting foam. The term "foaming agent" as used herein is intended to include both reactive materials such as water and inert materials such as halohydrocarbons which cause the reaction products to form an expanded foam.

In addition to the actual reactants and foaming agents it is also desirable in many cases to add a small amount of a surfactant in order to provide a more homogeneous mixture.

The following examples illustrate the use of our new compounds in forming flame resistant polyurethane foamed products.

Grams
100 — 3000 M.W. triol, product of oxypropylation of

-continued

| Grams | |
|---|---|
| | glycerol (Dow Voranol CP 3000) |
| 48.9 | — toluene diisocyanate (80% 2,4 isomer, 20% 2,6) |
| 10 | — product of Example 2 |
| 1.3 | — silicone surfactant (L-520 Union Carbide) |
| 3.7 | — water |
| 0.50 | — dimethylethanolamine |
| 0.20 | — trimethylaminoethylpiperazine |
| 0.70 | — 50% solution in dioctyl phthalate of stannous octoate. |

These ingredients yielded a flexible foam having a density of 2.01 lb/cu. ft. The foam was of good appearance, resiliency and cell size. The foam was self-extinguishing by ASTM test method D-1692. A similar foam prepared using 14 parts of tris(2-chloroethyl) phosphate which provides more phosphorus and more chlorine than the 10 grams of the product of Example 2, did not provide a foam with self-extinguishing properties. This is surprising inasmuch as fire retardance is generally dependent on the amount of phosphorus and chlorine added. Thus, only small amounts of the product of the invention are required to obtain desirable results, thereby avoiding urethane foam compounding problems generally encountered in using larger additive quantities.

It has also been found that the polycondensed product is a much more effective flame retardant agent than tris(2-chloroethylphosphate) when used in cellulose acetate. The amount utilized is dependent on composition, film thickness and degree of flame retardancy desired. Effective amounts can be easily determined by one skilled in the art. This is illustrated in the following example.

EXAMPLE 6

Cellulose acetate is dissolved in 80% acetone/20% ethanol to make a 20% solution. The product of Example 2 is dissolved in this solution and a 15 mil film is cast therefrom and dried at 80° C. Film containing 25% by weight of the product of Example 2 is self extinguishing when held vertically and ignited at the lower edge. This amount is less than that required to prepare a similar self extinguishing film using tris(2-chloroethyl) phosphate.

The preceding examples have illustrated the present invention using the (2-chloroethyl) phosphorus compound. With equal facility, (2-bromoethyl) phosphorus compounds can also be used therein.

It has also been found that the products of the present invention are not soluble in the normal dry cleaning fluids such as perchloroethylene, whereas tris(2-chloroethyl) phosphate is highly soluble. The polycondensed product of the present invention can therefore be coated onto various fabrics, such as cotton, to give fire retardant characteristics thereto, and also, the product can be incorporated into fiber forming compositions such as acetate rayon materials. In each case, the flame retardant agent would not be extractable by normal dry cleaning procedures. The products of the invention can also be used as additives to numerous polymer systems other than those mentioned hereinbefore as flame retardants and/or plasticizers such as to phenolics, acrylics, polystyrene, vinyl resins such as polyvinyl alcohol or polyvinyl chloride, polyesters, polyolefins, rubber, nitrocellulose, epoxy resins and the like. The compounds can also be used in paper and fabric coatings, and in asphalt, and in adhesives as flame retardant additives.

The invention is defined in the claims which follow.

What is claimed is:

1. A flame retardant composition comprising, in admixture, a polymeric material selected from the group consisting of polystyrene, polyolefines, vinyl polymers, rubber, nitrocellulose, epoxy resins, phenolic resins, acrylic resins, polyesters, cellulose acetate polymers, and polyurethane polymers in combination with liquid poly(chloroethylethyleneoxy) phosphoric acid esters which are prepared by reacting tris (2-chloroethyl) phosphate by heating said phosphate to a temperature within the range of from about 140° C. to about 220° C. in the presence of a basic catalyst with ethylene dichloride as reaction byproduct; and terminating said reaction at a reaction byproduct level of ethylene dichloride in an amount of from about 0.5 mole to about 0.9 mole ethylene dichloride per mole of tris(2-chloroethyl) phosphate in said reaction.

2. The flame retardant composition as recited in claim 1 wherein said polymeric material is a polyurethane.

3. The flame retardant composition as recited in claim 2 wherein said polyurethane comprises the reaction product of a polyisocyanate and polyoxyalkylene glycol.

4. The flame retardant composition as recited in claim 3 wherein said polyurethane is in the form of a foam.

5. The flame retardant composition of claim 1 which further includes the step of post-treating the liquid poly(chloroethylethyleneoxy) phosphoric acid esters with an alkylene oxide to neutralize the acidity in said esters.

6. A flame retardant composition comprising, in admixture, a cellulose acetate polymer in combination with liquid poly(chloroethylethyleneoxy)phosphoric acid esters which are prepared by reacting tris(2-chloroethyl) phosphate by heating said phosphate to a temperature within the range of from about 140° C. to about 220° C. in the presence of a basic catalyst with ethylene dichloride as reaction byproduct; and terminating said reaction at a reaction byproduct level of ethylene dichloride in an amount of from about 0.5 mole to about 0.9 mole ethylene dichloride per mole of tris(2-chloroethyl)phosphate in said reaction.

* * * * *

UNITED STATES PATENT AND TRADEMARK OFFICE
CERTIFICATE OF CORRECTION

PATENT NO. : 4,005,034
DATED : January 25, 1977
INVENTOR(S) : Edward D. Weil

It is certified that error appears in the above-identified patent and that said Letters Patent are hereby corrected as shown below:

Column 6, line 65, under "foamed products.", please insert:

EXAMPLE 5

A polyurethane foam was prepared utilizing the following composition:

Signed and Sealed this twelfth Day of July 1977

[SEAL]

Attest:

RUTH C. MASON
*Attesting Officer*

C. MARSHALL DANN
*Commissioner of Patents and Trademarks*